United States Patent
Iwanami

(10) Patent No.: US 12,059,256 B2
(45) Date of Patent: Aug. 13, 2024

(54) INFORMATION PROCESSING SYSTEM, INFORMATION PROCESSING METHOD, AND RECORDING MEDIUM

(71) Applicant: SONY CORPORATION, Tokyo (JP)

(72) Inventor: Hiroshi Iwanami, Tokyo (JP)

(73) Assignee: SONY CORPORATION, Tokyo (JP)

(*) Notice: Subject to any disclaimer, the term of this patent is extended or adjusted under 35 U.S.C. 154(b) by 808 days.

(21) Appl. No.: 17/052,738

(22) PCT Filed: Mar. 6, 2019

(86) PCT No.: PCT/JP2019/008731
§ 371 (c)(1),
(2) Date: Nov. 3, 2020

(87) PCT Pub. No.: WO2019/220745
PCT Pub. Date: Nov. 21, 2019

(65) Prior Publication Data
US 2021/0228129 A1    Jul. 29, 2021

(30) Foreign Application Priority Data

May 15, 2018   (JP) ................................ 2018-093564

(51) Int. Cl.
*A61B 5/16* (2006.01)
*G06F 3/01* (2006.01)

(52) U.S. Cl.
CPC .............. *A61B 5/165* (2013.01); *A61B 5/167* (2013.01); *G06F 3/011* (2013.01); *G06F 2203/011* (2013.01)

(58) Field of Classification Search
CPC ....... A61B 5/165; A61B 5/167; G06F 16/906; G06F 2203/011; G06F 3/011; G06Q 50/00; G06Q 50/10
See application file for complete search history.

(56) References Cited

U.S. PATENT DOCUMENTS

| | | | |
|---|---|---|---|
| 2007/0192038 A1* | 8/2007 | Kameyama | G06F 16/436 707/E17.143 |
| 2008/0269958 A1* | 10/2008 | Filev | A61B 5/4803 701/1 |
| 2016/0117597 A1 | 4/2016 | Ono et al. | |

FOREIGN PATENT DOCUMENTS

| | | |
|---|---|---|
| EP | 2923643 A1 | 9/2015 |
| JP | 2003-006316 A | 1/2003 |
| JP | 2005-258820 A | 9/2005 |
| JP | 2010-017403 A | 1/2010 |
| JP | 2010-110864 A | 5/2010 |

(Continued)

OTHER PUBLICATIONS

International Search Report and Written Opinion of PCT Application No. PCT/JP2019/008731, issued on May 28, 2019, 08 pages of ISRWO.

*Primary Examiner* — George Manuel
(74) *Attorney, Agent, or Firm* — CHIP LAW GROUP

(57) ABSTRACT

[Problem] To provide an information processing system, an information processing method, and a recording medium that can detect a worry and notify a user of a message. [Solution] An information processing system includes a control unit that performs control to estimate at least one of a worry cause of the user and a degree of worry of the user, and present a message to the user when at least one of the worry cause and the degree of worry satisfies a specific condition.

14 Claims, 12 Drawing Sheets

(56) References Cited

FOREIGN PATENT DOCUMENTS

| | | |
|---|---|---|
| JP | 2013-109575 A | 6/2013 |
| JP | 2017-220077 A | 12/2017 |
| WO | 2014/073612 A1 | 5/2014 |
| WO | 2014/080585 A1 | 5/2014 |
| WO | 2017/212783 A1 | 12/2017 |

\* cited by examiner

FIG.7

| No. | WORRY CAUSE | VALIDITY OF REALITY RECOGNITION | SOLVING POSSIBILITY | TYPE OF TRANSMISSION MESSAGE | BASIS |
|---|---|---|---|---|---|
| 1-1 | WORRY ABOUT BANKRUPTCY IN OLD AGE | INVALID | POSSIBLE | TYPE A | ·AMOUNT OF PENSION TO RECEIVE IS MUCH LARGER THAN AVERAGE<br>·POSSIBILITY OF BANKRUPTCY IS LOW BECAUSE OF ZERO DEBT AT THE TIME OF AGE 60 OR THE LIKE |
| 1-2 | WORRY ABOUT DEATH OF ILLNESS | INVALID | POSSIBLE | TYPE A | ·ALL NUMERICAL VALUES OF MEDICAL CHECKUP ARE NORMAL<br>·BEING HEALTHY BECAUSE OF WORKOUT OF MIDDLE LOAD LEVEL THREE TIMES A WEEK OR THE LIKE AND POSSIBILITY OF DEATH IS LOW IN PERSPECTIVE OF HEALTH |
| 1-3 | WORRY ABOUT BEING KILLED BY UNSPECIFIED NATURAL DISASTER OR ACCIDENT | VALID | IMPOSSIBLE | TYPE B | POSSIBILITY OF UNSPECIFIED DISASTER OR ACCIDENT IS NOT HIGH, BUT THERE IS CASE OF DYING. HUMAN IS NOT IMMORTAL. |
| ... | ... | ... | ... | ... | ... |
| 2-1 | SMALL INCOME | VALID | POSSIBLE | TYPE C | THERE IS CHOICE OF OBTAINING QUALIFICATION OR CHANGING JOB |
| 2-2 | INCONVENIENT COMMUTING BECAUSE OF LONG DISTANCE BETWEEN HOME AND STATION | VALID | POSSIBLE | TYPE C | ONLY HAVE TO MOVE |
| 2-3 | BAD ACADEMIC RESULTS OR BAD BEHAVIOR OF CHILD | VALID | POSSIBLE | TYPE C | TO BE IMPROVED BY MAKING CHILD GO CRAM SCHOOL OR IMPROVING FAMILY RELATIONSHIP |
| 2-4 | INSOLENT SUBORDINATE COMPLAINS | VALID | POSSIBLE | TYPE C | CORRESPOND BY IMPROVEMENT OF MANAGEMENT SKILL |
| ... | ... | ... | ... | ... | ... |
| 3-1 | WANT TO GET BACK TOGETHER WITH EX-GIRLFRIEND | INVALID | POSSIBLE | TYPE A | DEGREE OF DISLIKE OF GIRLFRIEND IS HIGH AND THINKING THAT GETTING BACK TOGETHER IS POSSIBLE IS WRONG REFLECTION OF REALITY |
| 3-2 | REGRET NOT BEING WITH PARENT WHEN HE/SHE PASSES AWAY | VALID | IMPOSSIBLE | TYPE B | UNCHANGEABLE BECAUSE IT IS PAST EVENT |
| 3-3 | IF I HAD STUDIED HARDER, I COULD HAVE ENTER THAT COLLEGE | VALID | IMPOSSIBLE | TYPE B | UNCHANGEABLE BECAUSE IT IS PAST EVENT |
| ... | ... | ... | ... | ... | ... |

FIG.8

| No. | WORRY CAUSE | VALIDITY OF REALITY RECOGNITION | SOLVING POSSIBILITY | TYPE OF TRANSMISSION MESSAGE | MESSAGE EXAMPLE |
|---|---|---|---|---|---|
| 1 | WORRY ABOUT BANKRUPTCY IN OLD AGE | INVALID | - | TYPE A | "WITH YOUR CURRENT FINANCIAL SITUATION, YOU DO NOT HAVE TO WORRY" |
| 2 | SAME AS ABOVE | VALID | IMPOSSIBLE | TYPE B | "GIVE UP AND THINK ABOUT RELYING ON FAMILY" |
| 3 | SAME AS ABOVE | VALID | POSSIBLE | TYPE C | "… (SILENT)", "HOW ABOUT SEARCHING JOB" |
| ⋮ | ⋮ | ⋮ | ⋮ | ⋮ | ⋮ |
| 7 | WORRY ABOUT BEING KILLED BY NATURAL DISASTER OR ACCIDENT | INVALID | - | TYPE A | "POSSIBILITY IS LOW. YOU DO NOT HAVE TO WORRY" |
| 8 | SAME AS ABOVE | VALID | IMPOSSIBLE | TYPE B | "IN CASE OF BAD LUCK, YOU NEED TO GIVE UP." |
| 9 | SAME AS ABOVE | VALID | POSSIBLE | TYPE C | "… (SILENT)", "HOW ABOUT THINKING ABOUT CHANGING JOB" |
| ⋮ | ⋮ | ⋮ | ⋮ | ⋮ | ⋮ |

FIG.12

| ID | PERSON WHO WORRIES | WORRY TYPE | WORRY TARGET | WORRY CAUSE | TYPE OF TRANSMISSION MESSAGE | MESSAGE EXAMPLE |
|---|---|---|---|---|---|---|
| 1 | USER A | TYPE a: MISUNDERSTANDING OR WRONG ASSUMPTION OF THE PERSON | USER B | "ALTHOUGH I AM KIND TO TELL IT, B DOES NOT HEAR WHAT I SAY! B IS INSOLENT." | TYPE A | "IT SEEMS THAT B TRIES TO WORK HARD BY HIMSELF/HERSELF" |
| 2 | USER B | TYPE a: MISUNDERSTANDING OR WRONG ASSUMPTION OF THE PERSON | USER A | "ALTHOUGH I AM WORKING SO HARD, A TALKS TO ME INSISTENTLY AND ANNOYINGLY. TOO ANNOYING!" | TYPE A | "IT SEEMS THAT A IS KIND TO TELL THAT" |
| 3 | USER A | TYPE b: CASE OF WORRY THAT CANNOT BE SOLVED BY EFFORTS OF THE PERSON | - | WORRY ABOUT DEATH FROM UNEXPECTED ACCIDENT | TYPE B | "WHAT DO YOU WANT BY WORRYING ABOUT SUCH THING" |
| 4 | USER B | TYPE a: MISUNDERSTANDING OR WRONG ASSUMPTION OF THE PERSON | USER F | I THINK SALES DOES NOT REACH GOAL SINCE F CAME WORKPLACE | TYPE A | "IT IS NOT CORRECT" |
| ⋮ | ⋮ | ⋮ | ⋮ | ⋮ | ⋮ | ⋮ |

INFORMATION PROCESSING SYSTEM, INFORMATION PROCESSING METHOD, AND RECORDING MEDIUM

CROSS REFERENCE TO RELATED APPLICATIONS

This application is a U.S. National Phase of International Patent Application No. PCT/JP2019/008731 filed on Mar. 6, 2019, which claims priority benefit of Japanese Patent Application No. JP 2018-093564 filed in the Japan Patent Office on May 15, 2018. Each of the above-referenced applications is hereby incorporated herein by reference in its entirety.

FIELD

The present disclosure relates to an information processing system, an information processing method, and a recording medium.

BACKGROUND

In recent years, with the development of information processing technology, an information presentation system that presents various kinds of information to users has been provided. With the downsizing of cameras and the improvement of information processing capabilities, an information presentation system has been proposed in which a user's situation (context) is grasped at any time by image recognition, sound recognition, biometric recognition, position information analysis, or the like to perform information presentation according to the user's situation.

Here, for example, Patent Literature 1 below proposes a technology in which an emotional expression expressing an emotion is detected from text data described by a person who can be a target person of mental care (emotional polarity is determined by morphological analysis), and if it is negative, response is performed to comfort the person or ask about basis, and if it is positive, response is performed in a coordinated or cooperative manner.

Patent Literature 2 below discloses performing interaction operation according to a user's internal state including a user's voice, biometric information such as a pulse, and a user's mental state such as a tense state or a pleasant state.

Patent Literature 3 below discloses a technology of issuing a negative warning by a warning agent when a driver is uncomfortable, and showing empathy by an advisory agent to guide the driver to drive safely.

Patent Literature 4 below discloses classifying physical state and psychological state of a user into positive and negative, and generating a conversational sentence of comfort, synchronization or the like.

CITATION LIST

Patent Literature

Patent Literature 1: JP 2013-109575 A
Patent Literature 2: JP 2010-110864 A
Patent Literature 3: JP 2005-258820 A
Patent Literature 4: WO 14/073612 A

SUMMARY

Technical Problem

However, the related art does not mention detecting a situation in which a user has some worry.

In view of this, the present disclosure proposes an information processing system, an information processing method, and a recording medium that can detect a worry and notify a user of a message.

Solution to Problem

According to the present disclosure, an information processing system is proposed. The an information processing system includes a control unit that performs control to estimate at least one of a worry cause of a user and a degree of worry of the user based on sensing data related to the user, and present a message to the user when at least one of the worry cause and the degree of worry satisfies a specific condition.

According to the present disclosure, an information processing method by a processor is proposed. The information processing method includes performing control to estimate at least one of a worry cause of a user and a degree of worry of the user based on sensing data related to the user, and present a message to the user when at least one of the worry cause and the degree of worry satisfies a specific condition.

According to the present disclosure, a recording medium in which a program is recorded is proposed. The program causes a computer to function as a control unit that performs control to estimate at least one of a worry cause of a user and a degree of worry of the user based on sensing data related to the user, and present a message to the user when at least one of the worry cause and the degree of worry satisfies a specific condition.

Advantageous Effects of Invention

As described above, according to the present disclosure, it is possible to detect a worry and notify a user of a message.

Note that the above-described effect is not necessarily limitative. With or in place of the above effect, there may be achieved any one of the effects described in this specification or other effects that may be grasped from this specification.

BRIEF DESCRIPTION OF DRAWINGS

FIG. 7 is a diagram illustrating an example of a data configuration of worry classification table data according to the second embodiment.

FIG. 8 is a diagram illustrating an example of a data configuration of a message example according to the worry classification according to the second embodiment.

FIG. 12 is a diagram illustrating worry types and corresponding message examples according to the fifth embodiment.

DESCRIPTION OF EMBODIMENTS

Favorable embodiments of the present disclosure will be described in detail with reference to the appended drawings. Note that, in the present specification and drawings, redundant description of a configuration element having substantially the same functional configuration is omitted by providing the same sign.

Further, the description will be made in the following order.

1. Overview of information processing system according to an embodiment of the present disclosure 2. Configuration
2-1. Configuration of information processing terminal 1
2-2. Configuration of server 2
3. Embodiments
3-1. First embodiment
3-2. Second embodiment
3-3. Third embodiment
3-4. Fourth embodiment
3-5. Fifth embodiment
3-6. Supplement
4. Summary

1. OVERVIEW OF INFORMATION PROCESSING SYSTEM ACCORDING TO ONE EMBODIMENT OF PRESENT DISCLOSURE

Figure 1:
FIG. 1 is a diagram describing an overview of an information processing system according to an embodiment of the present disclosure.

FIG. 1 is a diagram describing an overview of an information processing system according to an embodiment of the present disclosure. As illustrated in FIG. 1, the information processing system according to the present embodiment is an agent system capable of detecting a user's worry and notifying the user of a message.

Generally speaking, a worry of a person can be said as having some trouble and searching for a solution to the trouble. There is no need to worry if a person knows a solution, but in a case where a person does not know what kind of solution is good, a solution still needs to be searched, so that a person gets in a negative situation of worrying.

Here, worries include meaningful worries and meaningless worries.

For example,
Worries that the person is searching for a solution after correctly understanding the current situation
Worries that can be solved to some extent by the efforts of the person
and the like can be categorized as meaningful worries because it will lead to growth as a person by carefully thinking out what kind of solution is the best, and provide a sense of achievement when the person finds a solution.

On the other hand,
Worries that the person is looking for a solution based on incorrect recognition of the current situation
Worries that cannot be solved only by the efforts of the person
and the like are originally meaningless worries, but a situation is assumed where the person who is worry about that is not aware of the fact. In such a case, it may happen that the person will continue to worry. When a person worries, the person is worry about something, and feels strong "anxiety", "fear", and "despair", and such a mental state is not said to be a stable mental state and is not preferable.

To such user's worry, it is useless to worry by "incorrect recognition of the current situation" or "things that cannot be solved by the efforts of the person" (a thing for which solution cannot be found even though the person is worried about it), and it is important to correctly recognize the current situation.

Correctly recognizing the current situation means "clearly looking at" things and causal reasons, and for example, there is a teaching in the world of Buddhism of "see clearly causal reasons" using the word "resignation". When a problem occurs, a person can correctly look back on the cause, and in some cases, clearly see where a reason is, and repeat deep reflection and improvement to grow.

In view of this, the present embodiment proposes an agent system capable of detecting the worry cause or the degree of worry as a worry situation and notifying a user of an appropriate message according to the worry cause or the degree of worry. More specifically, proposed is an agent system capable of helping to correctly recognize the current situation and helping to get out of a thing that is useless to worry about.

The worry situation of the user can be detected from gestures, verbal behaviors, body reactions, sleep situations, and the like. The details will be described subsequently.

Figure 2:
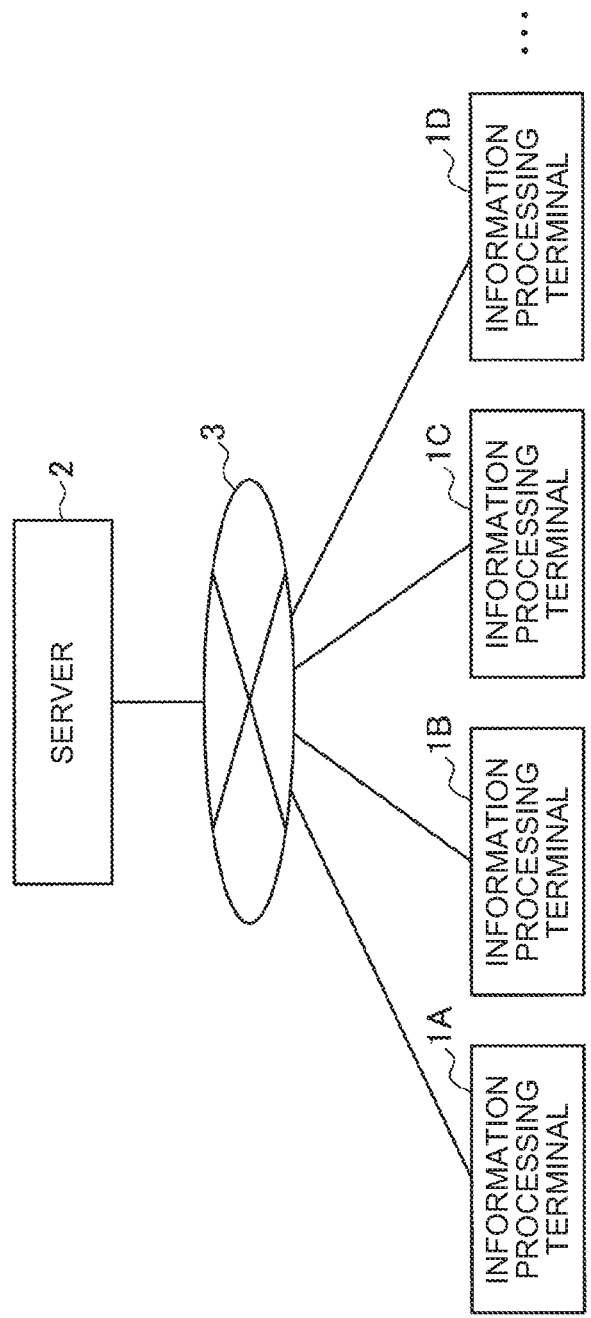
FIG. 2 is a diagram illustrating an example of an overall configuration of the information processing system according to the present embodiment.

Subsequently, an entire configuration of an information processing system according to the present embodiment as described above will be described with reference to FIG. 2. FIG. 2 is a diagram illustrating an example of an entire configuration of the information processing system according to the present embodiment.

As illustrated in FIG. 2, the information processing system according to the present embodiment includes an information processing terminal 1 (1A to 1D . . . ) used by each user, and a server 2. The information processing terminal 1 and the server 2 can be connected via a network 3. The information processing terminal 1 may be a smartphone, a mobile phone, a PC, or a wearable device (head mounted display (HMD) such as glasses type, smart watch, smart band, smart earphone, smart neck, or the like), or a dedicated terminal such as a stationary type speaker device. The information processing terminal 1 transmits data (camera image, sound data, biometric data, or the like) sensed from the user by each sensor to the server 2.

The server 2 is an agent server that detects a worry situation on the basis of user sensing data and notifies a message according to the worry situation. Specifically, the server 2 detects the degree of worry and estimates the worry cause, and outputs a message according to the degree of worry and the worry cause to the information processing terminal 1. The message of which the user is notified is not limited to presentation of the solution to the worry, and includes a message for causing the user to notice that the user does not correctly recognize the current situation, and that it is useless to worry about, and helping the user to get out of the useless worry.

The information processing system according to the embodiment of the present disclosure has been described hereinabove. Next, a specific configuration of each apparatus included in the information processing system according to the present embodiment will be described with reference to the drawings.

2. CONFIGURATION

<2-1. Configuration of Information Processing Terminal 1>

Figure 3:
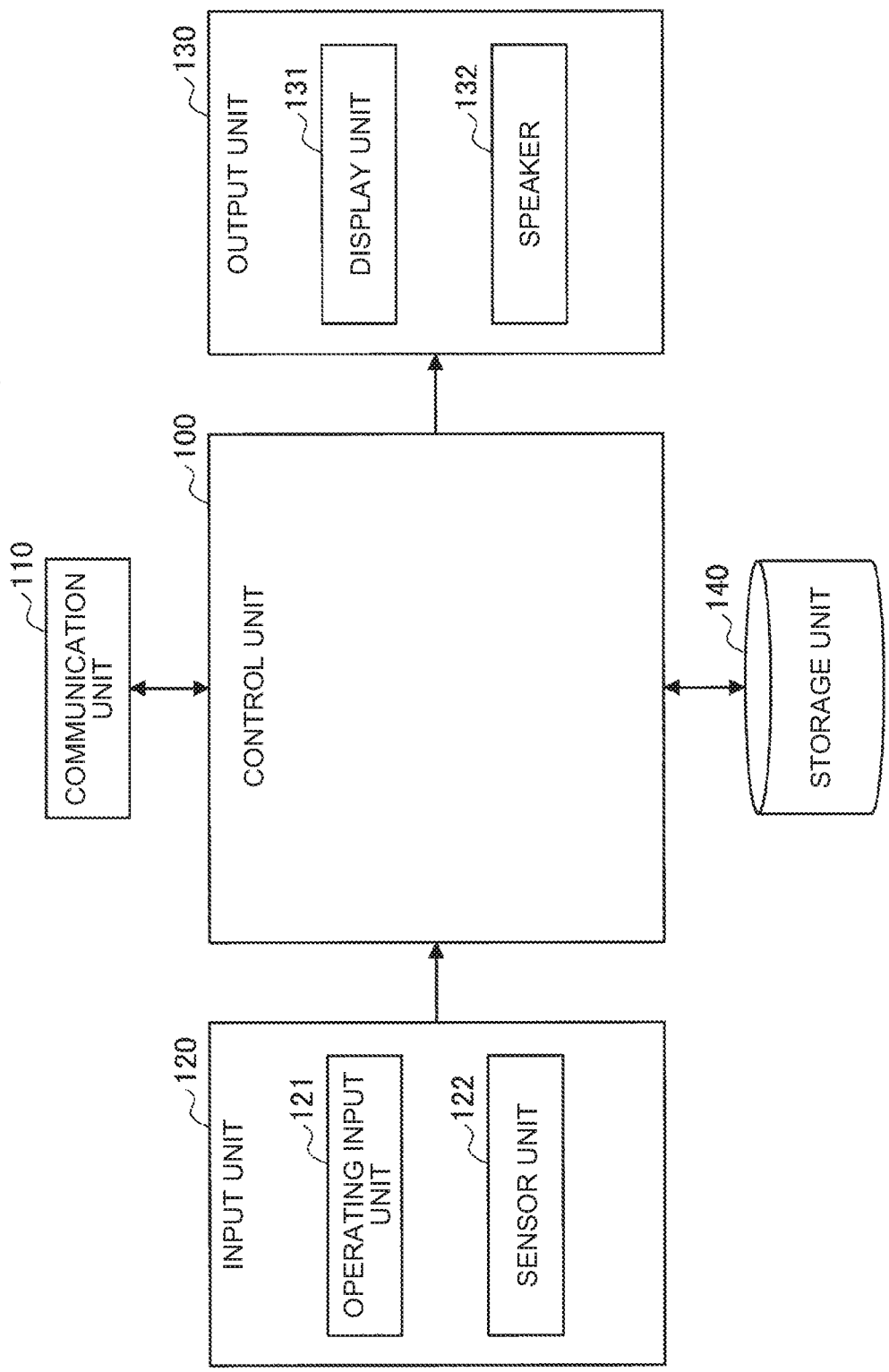
FIG. 3 is a block diagram for explaining an example of a configuration of an information processing terminal according to the present embodiment.

FIG. 3 is a block diagram illustrating an example of the configuration of the information processing terminal 1 according to the present embodiment. As illustrated in FIG. 3, the information processing terminal 1 includes a control unit 100, a communication unit 110, an input unit 120, an output unit 130, and a storage unit 140.

The control unit 100 functions as an arithmetic processing device and a control device, and controls the overall operation of the information processing terminal 1 according to various programs. The control unit 100 is realized by an electronic circuit such as a central processing unit (CPU) or a microprocessor, for example. Further, the control unit 100 may include a read only memory (ROM) that stores a program, a calculation parameter, or the like to use, and may include a random access memory (RAM) that temporarily stores a parameter or the like which changes as appropriate.

The control unit 100 according to the present embodiment can perform control of transmitting, from the communication unit 110 to the server 2, sensing data acquired from a sensor 122, and control of outputting information received from the server 2 via the communication unit 110 from the output unit 130. The control unit 100 can perform analysis of various types of sensing data (sound recognition, biometric data analysis, object recognition based on camera images and distance measurement data, movement state recognition, facial expression analysis, motion analysis, posture recognition, face recognition, line of sight recognition or the like).

(Communication Unit 110)

The communication unit 110 is connected to the network 3 in a wired or wireless manner, and transmits and receives data to and from the server 2 in the network. The communication unit 110 is communicably connected to the network 3 by, for example, a wired/wireless local area network (LAN), Wi-Fi (registered trademark), Bluetooth (registered trademark), long term evolution (LTE), third generation mobile communication system (3G), or the like.

(Input Unit 120)

The input unit 120 has an operating input unit 121 and a sensor 122, and inputs information acquired from the operating input unit 121 or the sensor 122 to the control unit 100. The operating input unit 121 detects an operation input by the user on the information processing terminal 1. The operating input unit 121 may be, for example, a touch sensor, a pressure sensor, or a proximity sensor, or may be a physical configuration such as a button, a switch, and a lever.

The sensor 122 is of various types that senses the user situation or the surrounding environment, and inputs the sensed data to the control unit 100. The sensor 122 is assumed to be, for example, a positioning unit (outdoor positioning using a global positioning system (GPS) or the like, or indoor positioning using Bluetooth, Wi-Fi, or the like), a camera, a microphone (hereinafter, referred to as microphone), a ranging sensor, a thermo sensor (for example, installed in a stationary projector to measure the user's body temperature), an ultrasonic sensor, a motion sensor (for example, acceleration sensor, gyro sensor, geomagnetic sensor, or the like), biological sensor (for example, body temperature, vein, pulse, heartbeat, respiration, sweating, blood pressure, EEG, electrooculogram, myoelectric value, eye movement, gaze detection, or the like), an environmental sensor (for example, illuminance, temperature, humidity, or the like).

(Output Unit 130)

The output unit 130 is a presentation unit that presents information to the user under the control of the control unit 100. The output unit 130 has a display unit 131 and a speaker 132. The display unit 131 may be a display unit implemented by a liquid crystal display (LCD) device, an organic light emitting diode (OLED) device, or the like. The display unit 131 may be a so-called optical see-through display having optical transparency. Further, the display unit 131 may be a projector.

The speaker 132 reproduces a sound signal according to the control of the control unit 100. The speaker 132 may be a directional speaker, for example. By using a directional speaker, only the user can hear agent sound.

(Storage Unit 140)

A storage unit 140 is realized by a read only memory (ROM) that stores the program, the calculation parameter, or the like to be used for processing by the control unit 100, and a random access memory (RAM) that temporarily stores the parameter or the like which changes as appropriate.

The configuration example of the information processing terminal 1 according to the present embodiment has been specifically described above. Note that the configuration of the information processing terminal 1 is not limited to the example illustrated in FIG. 3, and for example, the information processing terminal 1 may be configured by a plurality of devices, or an external sensor (a sensor device provided on the environment side or sensing data may be acquired from a sensor device or a sensor device that the user separately wears).

<2-2. Configuration of Server 2>

Figure 4:
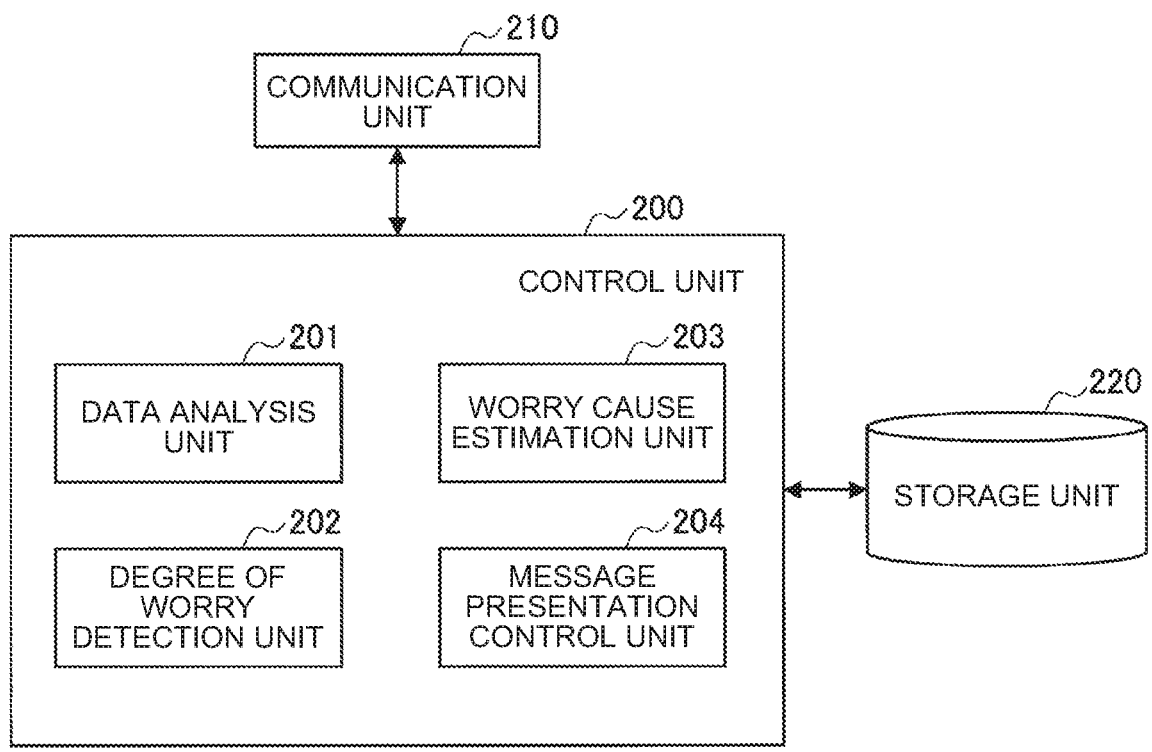
FIG. 4 is a block diagram for explaining an example of a configuration of a server according to the present embodiment.

Subsequently, a configuration of the server 2 will be described with reference to FIG. 4. FIG. 4 is a block diagram illustrating an example of a configuration of the server 2 according to the present embodiment. As illustrated in FIG. 4, the server 2 (information processing device) includes a control unit 200, a communication unit 210, and a storage unit 220.

(Control Unit 200)

The control unit 200 functions as an arithmetic processing device and a control device, and generally controls an operation in the server 2 according to various programs. The control unit 200 is realized by, for example, an electronic circuit such as a Central Processing Unit (CPU), a microprocessor or the like. Further, the control unit 200 may include a read only memory (ROM) that stores a program, a calculation parameter, or the like to use, and may include a random access memory (RAM) that temporarily stores a parameter or the like which changes as appropriate.

Further, the control unit 200 according to the present embodiment also functions as a data analysis unit 201, a degree of worry detection unit 202, a worry cause estimation unit 203, and a message presentation control unit 204.

The data analysis unit 201 analyzes the sensing data acquired from the information processing terminal 1. For example, the data analysis unit 201 extracts the feature amount of the gesture of the user, the feature amount of the verbal behavior, the feature amount of the biological reaction, the feature amount of the sleep situation, and the like. Specifically, for example, the following feature amount can be extracted.

TABLE 1

Gesture feature amount
Hold his/her head
Frown
Sigh
Look at one point and remain still for long time
Not respond when spoken by person
Knock desk
Frequency of shaking legs
Touch or pull own hair
. . .

TABLE 2

Verbal behavior feature amount
Speak specific negative words
"all over", "what should I do?", "I'm in trouble" or the like
Speak specific attack words
"fuck", "damn it", "idiot" or the like
Try to say, rethink about it and give up
Speaking volume becomes large
Speaking volume becomes small
Harsh tone
. . .

The degree of worry detection unit 202 detects the degree of worry of the user on the basis of the data analysis result. For example, the degree of worry detection unit 202 detects the degree of worry (at least a situation where the user worries about something) on the basis of the feature amount of the gesture of the user, the feature amount of the verbal behavior, the feature amount of the biological reaction, or the feature amount of the sleep situation that has been analyzed. Details will be described later in each embodiment.

The worry cause estimation unit 203 estimates the worry cause of the user on the basis of the data analysis result. For example, the degree of worry detection unit 202 estimates the worry cause on the basis of the user gesture (motion, sigh, behavior, or the like), verbal behavior (conversation, soliloquy, or the like), Internet search history, posted content to social networks, or the like that has been analyzed. At this time, the worry cause estimation unit 203 may perform worry estimation by referring to a worry classification list prepared in advance. Details will be described later in each embodiment.

The message presentation control unit 204 extracts, for example, from a message database prepared in advance, or automatically creates a message of an appropriate type according to the detected degree of worry or the estimated type of the worry cause, and performs control to present the message to the user. The presentation of the message may be performed by sound or image (text). The worry of a person can be classified as follows.

(1) Useless worry that cannot be solved even if the person makes an effort
(2) Useless worry because the person's misunderstanding or belief is the cause
(3) Meaningful worry that can be solved by the effort of the person and the person correctly recognizes the situation The message presentation control unit 204 sends out a message of a type according to each such classification. For example, in the case of type (1), a message to the user to accept the reality (a message that tells the user not to worry because it is useless) is given, in the case of (2), a message that points out the user's beliefs or misunderstandings (a message that encourages the user to correctly recognize reality) is given, and in the case of (3), any message is given because it is worth worrying, or a message of advice level as a hint for solution is given.

(Communication Unit 210)

The communication unit 210 is connected to the network 3 in a wire or wireless manner, and transmits and receives data to and from each information processing terminal 1 through the network 3. The communication unit 210 is communication-connected to the network 3 through, for example, a wired/wireless local area network (LAN), Bluetooth, or wireless fidelity (Wi-Fi (registered trademark)).

(Storage Unit 220)

The storage unit 220 is realized by a ROM that stores programs, calculation parameters, or the like used for the processing of the control unit 200, and a RAM that temporarily stores parameters varying as appropriate. For example, the storage unit 220 according to the present embodiment may store a history of user sensing data, worry classification table data, message data by type, and the like.

The configuration of the server 2 according to the present embodiment has been specifically described hereinabove. Note that the configuration of the server 2 illustrated in FIG. 4 is an example, and the present embodiment is not limited thereto. For example, at least some of configurations of the server 2 may be in an external apparatus, or at least some of respective functions of the control unit 200 may be realized by the information processing terminal 1, an edge server, and the like. In addition, each configuration of the control unit 200 illustrated in FIG. 4 and the storage unit 140 are all provided in the information processing terminal 1, and presentation of the message according to the worry situation of the user may be executed by the application of the information processing terminal 1.

3. EMBODIMENTS

Subsequently, embodiments of the information processing system according to the present embodiment will be described in detail with reference to the drawings.

3-1. First Embodiment

In the first embodiment, an appropriate message is notified according to the situation in which the user worries (degree of worry and worry cause).

For example, the gestures of the user such as sighing or holding the head when the user who hurt feelings of a girlfriend by a small word and was dumped by the girlfriend looks at past photos on a smartphone, PC, or the like (information processing terminal 1), and see a photograph of the girlfriend, are sensed by an inside camera of the smartphone or a camera of the PC and the worry situation is detected by the server 2. The server 2 estimates the worry cause and presents an appropriate message when such a behavior is performed the certain number of times or more. Specifically, the server 2 estimates that the user worries because the user wants to get back together with the girlfriend on the basis of the user's gestures or the like, determines that it is a worry that cannot be solved by the effort of the person, or a worry that the user does not correctly recognize the current situation (that she hates the user), and performs control to present a message such as "let's forget about it" urging that it is useless to worry about to the user from the information processing terminal 1.

Such operation processing of the present embodiment will be specifically described below with reference to FIG. 5.

Figure 5:
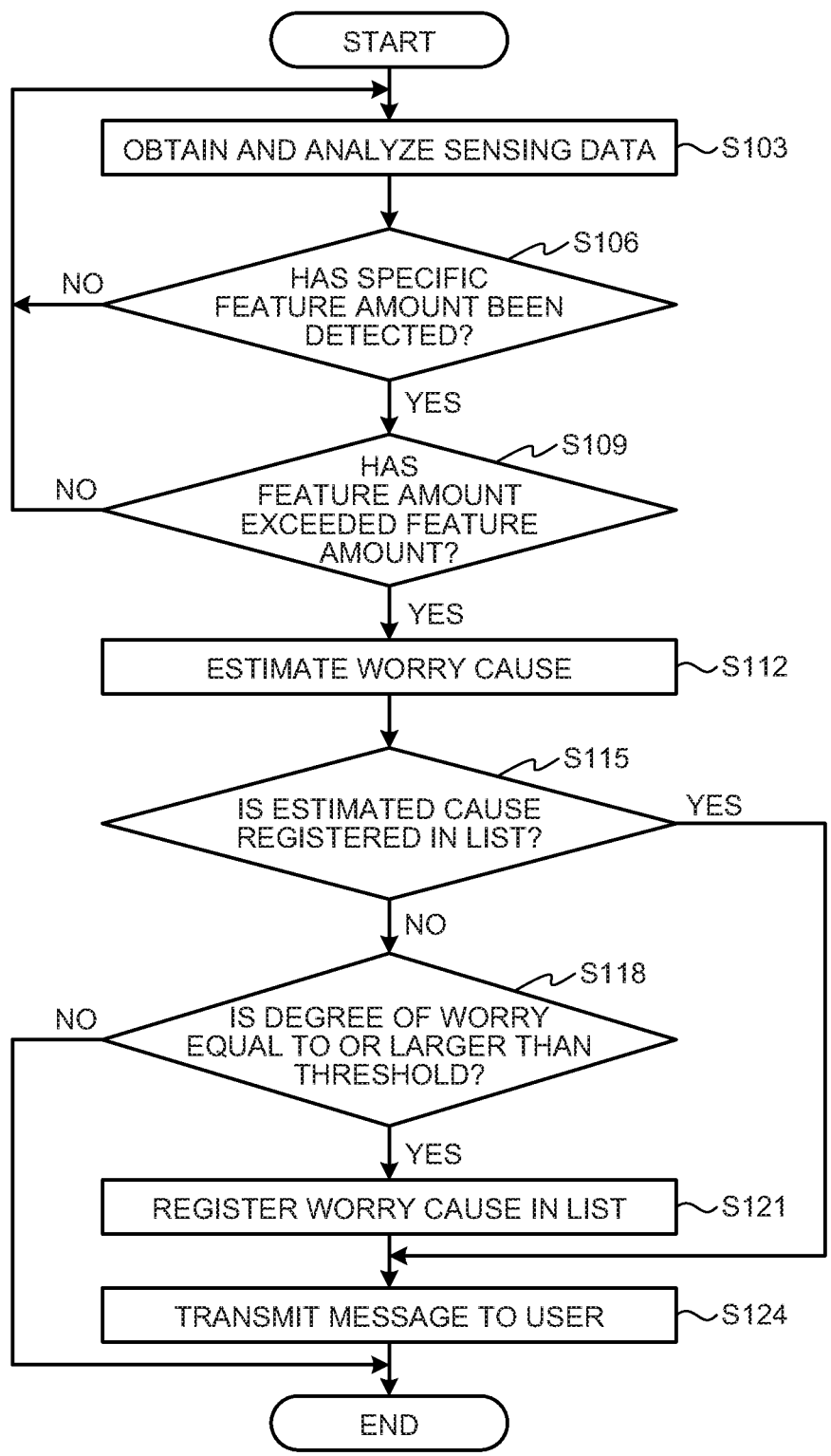
FIG. 5 is a flowchart illustrating an example of operation processing according to a first embodiment.

FIG. 5 is a flowchart illustrating an example of operation processing according to the present embodiment.

As illustrated in FIG. 5, first, the server 2 acquires the sensing data detected by the information processing terminal 1, and analyzes the data by the data analysis unit 201 (step S103). More specifically, the data analysis unit 201 analyzes the user's gesture, verbal behavior, biological reaction, sleep situation, and the like. Specific feature amounts are as indicated in Tables 3 to 6 below. The items illustrated in Tables 3 to 6 are a list obtained by investigating and listing amounts of features that a person generally indicates when the person worries in advance.

The specific examples of "gesture" are as described above (sighing, holding the head, or the like when looking at a picture of the girlfriend that the user broke up with), and "verbal behavior" is assumed to be unintentionally saying "shit", or suddenly speaking harshly when the person hears the name of the girlfriend that is spoken casually.

The gesture is a feature amount obtained mainly by analyzing image information from a camera. For example, the gesture is obtained from a front camera of a smartphone or a PC carried by an individual, or a camera installed in a room, or the like. Further, the verbal behavior is mainly obtained from a microphone of a smartphone or a PC, a microphone installed in a room, or the like. The biological signal can be sensed from a wearable device worn by the user, and the sleep situation can be obtained from a sensor installed on a bed or a sensor of a smartphone placed on a bedside.

Next, the worry cause estimation unit 203 of the server 2 detects a specific feature amount by data analysis (step S106/Yes), and when the feature amount exceeds a predetermined threshold (step S109/Yes), the worry cause is estimated (step S112). That is, when the detection of the specific feature amount exceeds the threshold, it can be said that the user's anxiety (anxiety level) is equal to or more than a certain level.

Here, the following data can be given as an example of the detected specific feature amount and the predetermined threshold.

TABLE 3

| No. | Gesture feature amount | Threshold |
| --- | --- | --- |
| 1-1 | Hold his/her head | Three times or more per hour |
| 1-2 | Frown | Three times or more per hour |
| 1-3 | Sigh | Five times or more per day |
| 2-1 | Look at one point and remain still for long time | 30 minutes or more in total per day |
| 2-2 | Not respond when spoken by person | Three times or more per day |
| 3-1 | Knock desk | 30 minutes or more in total per day |
| 3-2 | Frequency of shaking legs | 30 minutes or more in total per day |
| 3-3 | Touch or pull own hair | One hour or more in total per day |
| ... | ... | ... |

TABLE 4

| No. | Verbal behavior feature amount | Threshold |
| --- | --- | --- |
| 1-1 | Speak specific negative words "all over", "what should I do?", "I'm in trouble" or the like | Ten times or more per day |

TABLE 4-continued

| No. | Verbal behavior feature amount | Threshold |
| --- | --- | --- |
| 1-2 | Speak specific attack words "fuck", "damn it", "idiot" or the like | Five times or more per day |
| 2-1 | Try to say, rethink about it and give up | Three times per day |
| 3-1 | Speaking volume becomes large | Double or more as compared to normal |
| 3-2 | Speaking volume becomes small | ½ or less as compared to normal |
| 3-3 | Harsh tone | Double or more as compared to normal |
| ... | ... | |

TABLE 5

| No. | Biological reaction feature amount | Threshold |
| --- | --- | --- |
| 1-1 | Increase in cortisol level in sweat or blood | Healthy person standard value or more |
| 2-1 | Decrease in weight | 20% or more decrease |
| ... | ... | |

TABLE 6

| No. | Sleeping situation feature amount | Threshold |
| --- | --- | --- |
| 1-1 | Time to initiation of sleep | One hour or more |
| 2-1 | Number of times of rolling over | Double or more as compared to normal |
| ... | ... | |

Note that the feature amount may be used alone for determination, but a plurality of feature amounts may be combined for determination. For example, when the user sees a photograph of the girlfriend, the reaction appears in the behavior, the verbal behavior, and the biological reaction, and it is strengthened by recording a plurality of features of the worry for the content, that is, the girlfriend. As a large amount of data is acquired, the frequency of observed feature amounts increases with respect to major concerns for the user, which may cause a statistical difference from the others.

Further, the worry cause estimation unit 203 can estimate the worry cause and more detailed situation and background from the gesture and verbal behavior of the user when the specific feature amount is detected, the email content entered by the user, the posted content to the social media, schedule information, diary, or the like. For example, when the user looks at a photograph of the girlfriend and sighs, it can be guessed that the girlfriend is the worry cause, but when they broke up and its background can be obtained from the language information such as the email content. Further, it is also possible for the agent to ask the user a question (for example, "Did you have anything with your girlfriend?") to obtain the detailed cause, situation, background, or the like.

Next, the message presentation control unit 204 determines whether or not the subject of the estimated worry cause is registered in the worry subject list (not illustrated) that is listed in advance as the worry cause subject of which message is to be notified. (Step S115). In the worry subject list, worry subjects of which message is to be notified such as lovers, parents, families, relatives, work, relationships, health, and money are registered.

Next, when the worry subject is not registered in the list (Step S115/No), the control unit 200 determines whether or not to newly register the worry subject estimated this time, on the basis of whether or not the degree of worry is equal to or larger than a threshold (Step S118). Here, Table 7 below illustrates an example of the threshold for determining whether or not to newly register the worry subject in the list. For example, when the feature amounts in Tables 3 to 6 described above exceed the threshold illustrated in Tables 3 to 6 by a certain amount or more as described below, it may be determined that the worry cause is registered in the list.

TABLE 7

| Worry cause (subject) | Threshold of list registration |
|---|---|
| Having difficulty with girlfriend | 1.1 times |
| Relationship with parents | 1.1 times |
| Anxiety about old age | 1.1 times |
| ... | |

Next, when the degree of worry is equal to or larger than the threshold value (Step S118/Yes), the control unit 200 registers the worry cause in the worry cause subject list (Step S121).

Next, when the estimated cause is registered in the worry cause subject list (Step S115/Yes), or if the degree of worry is equal to or larger than a threshold (Step S118/Yes), the message presentation control unit 204 notifies the user of an appropriate message (a message for stopping worries, a message for advice, or the like) according to the worry (Step S124).

On the other hand, when the estimated cause is not registered in the worry cause subject list (Step S115/No), and if the degree of worry is below the threshold (Step S118/No), the message presentation control unit 204 does not notify a message.

The operation processing of the first embodiment has been specifically described above.

3-2. Second Embodiment

In the second embodiment, the worry cause of the user is classified, and a message of a type according to the classification is notified.

Figure 6:
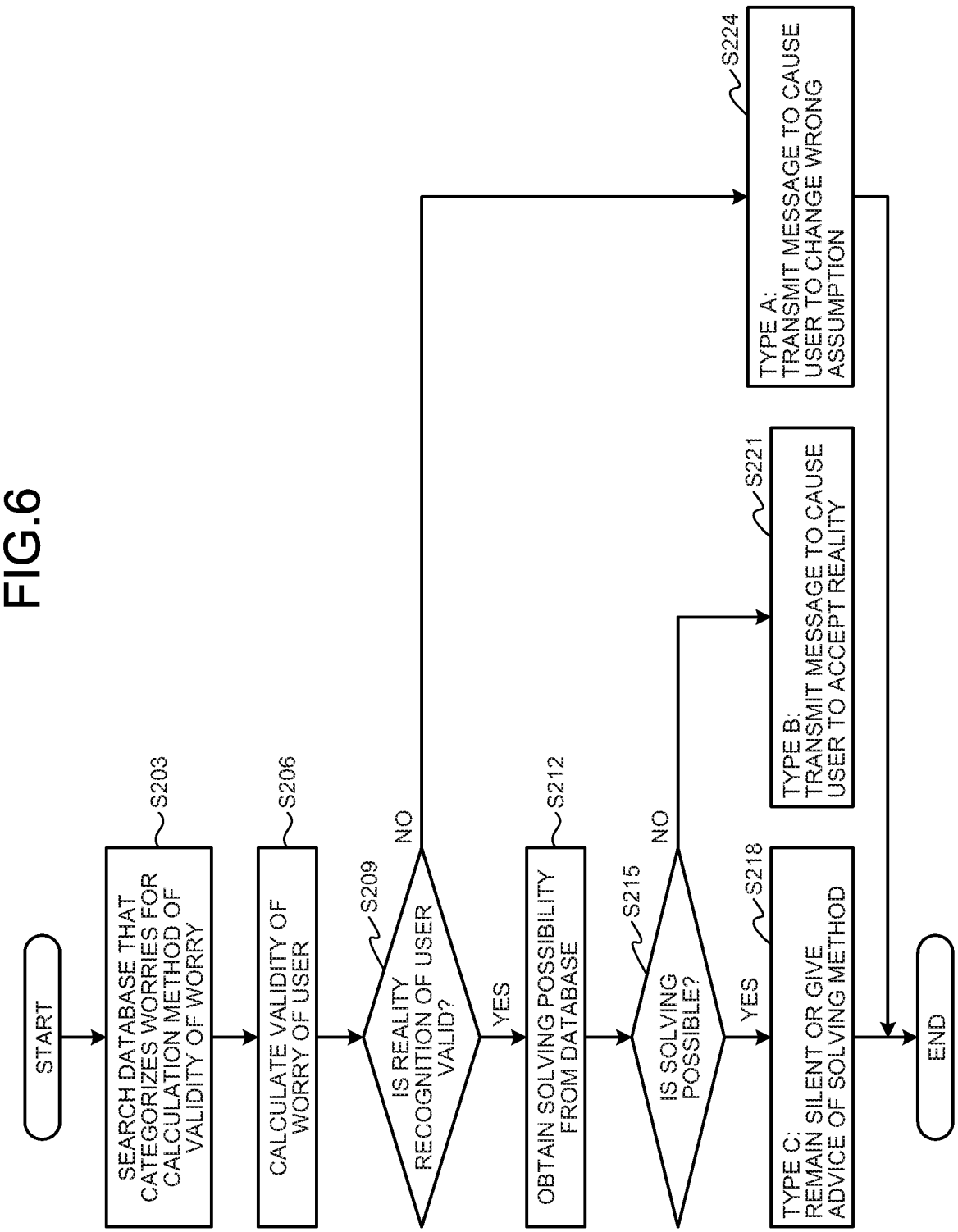
FIG. 6 is a flowchart illustrating an example of operation processing according to a second embodiment.

FIG. 6 is a flowchart illustrating an example of operation processing according to the present embodiment. The processing illustrated in FIG. 6 mainly corresponds to the processing of determining the content of the message to be transmitted to the user illustrated in Step 124 of FIG. 5 described in the first embodiment.

As illustrated in FIG. 6, first, the control unit 200 of the server 2 searches a database that categorizes worries (worry classification table data) for a calculation method of the validity of worry (Step S203). Here, FIG. 7 illustrates an example of the worry classification table data according to the present embodiment. The table illustrated in FIG. 7 illustrates an example of validity of reality recognition of the worry cause and its basis (calculation method of validity of worry).

For example, when the user is worried about bankruptcy in old age, regarding whether or not bankruptcy occurs in old age, the control unit 200 can create a prediction graph for the amount of wealth and the age at that time on the basis of the person's annual income, expected years of service, the existence of retirement allowance, the state of household spending for one month, or the like, and on the basis of the graph, calculate the validity of the worry about bankruptcy in old age (validity of reality recognition).

Further, when the user is worried about being killed due to an unspecified natural disaster or accident, since the possibility of being killed due to natural disaster or accident is small, but not zero, the control unit 200 determines that the worry has validity.

Further, when the user is distant from the station and worries about inconvenience commuting, the control unit 200 compares the distance between the user's home and the nearest station with, for example, the average distance between a home to a station in the same area, and determines the validity.

Note that, here, as an example, the method of obtaining the validity of the worry is registered in the database in advance, but the present embodiment is not limited to this. For example, data may be already given that indicates the degree of the validity in the specific worry and specific situation by opinions of a large number of people or experts. Further, after the event has occurred, a questionnaire may be taken to the majority of people and the number of votes may be used to determine whether the worry is valid.

Next, when the user's reality recognition is valid (the worry is correct) (Step S209/Yes), the message presentation control unit 204 obtains the solution possibility from the database (Step S212), and determines whether or not the worry can be solved (Step S215). The solving possibility is determined as possible when the worry can be solved by the effort of the person. An example of the solving possibility for the worry cause is as illustrated in FIG. 7.

Next, when the worry can be solved (Step S215/Yes), the message presentation control unit 204 determines that the worry is worth worrying, and keeps silent (no message), or notifies a message of type C that gives advice (hint) of the solution (Step S218). For example, when the user is worried about inconvenient commuting because the home is far from the station, if the problem is valid and can be solved by the effort of the person (moving or the like), a message of "Please think about it by yourself", "If it's that hard, why not look for a real estate property near the station?" or the like is notified. When the worry can be solved by the effort of the person, it is better to refrain from giving all advice for that person's growth, but it is assumed that there are some users who want a suggestion, whether or not to give advice may be determined depending on their personality and preferences.

On the other hand, when the worry cannot be solved by the effort of the person (Step S215/No), the message presentation control unit 204 notifies a message of type B that causes the user to accept the reality (Step S221). For example, when the user is worried about being killed due to a natural disaster or accident, since the possibility of being killed due to a natural disaster or accident is small, but not zero, this worry is valid but cannot be solved by the effort of the person, so that the message presentation control unit 204 notifies a message of, for example, "there is a case of being killed by an unspecified disaster or accident, but the probability is low. Don't worry. But a human is not immortal."

Further, when the user's reality recognition is not valid (Step S209/No), the message presentation control unit 204 notifies a message of type A that causes the user to change his/her belief (Step S224). For example, when the user is worried about bankruptcy in old age, when the validity of the worry is low (that is, the user's reality recognition is not correct) from calculation from the person's annual income, expected years of service, the existence of retirement allowance, the state of household spending for one month, or the like, the message presentation control unit 204 may notifies a message of type A that causes the user to change his/her belief, that is, for example, "With your current financial situation, you do not have to worry."

An example of each type of message notified to such a user is illustrated in FIG. 8. In the No. 1 to 3 examples illustrated in FIG. 8, for a person who is worried about bankruptcy in old age, for example, by checking the person's savings situation and the existence of debt, when the possibility of bankruptcy is low, the message presentation control unit 204 transmits a message of type A such as "With your current economic state, you do not have to worry", assuming that the reality recognition is wrong. On the other hand, when the possibility of bankruptcy is higher than the average from the savings situation, the existence of debt, and the like, the reality recognition is determined as valid. In this case, when the reality recognition is valid, and for example, when the person is difficult to work because of old age, the message presentation control unit 204 transmits a message of type B to cause the user to accept reality, give up on independence, and rely on a child or think about welfare. On the other hand, when the person can still work sufficiently and can solve the problem by himself/herself, the message presentation control unit 204 does nothing or transmits a message of advice for job searching.

Further, in the examples of No. 7 to 9 illustrated in FIG. 8, to a person who is worried about being killed in a natural disaster or accident, unless the person has a special dangerous work or has a hobby with danger, the message presentation control unit 204 determines that the reality recognition is wrong, and transmits a message of type A such as "The probability is low. You don't have to worry." On the other hand, for example, when the person has a dangerous work and the worry cannot be changed by the effort of the person, the message presentation control unit 204 transmits a message of "If you are unlucky, you have to give up." Further, if the person has a choice, the message presentation control unit 204 transmits a message of type C that advises to change the job.

The operation processing of the second embodiment has been specifically described above.

3-3. Third Embodiment

In a third embodiment, the power of social media is used to classify the cause of the user's worry and notify a message of a type according to the classification.

Figure 9:
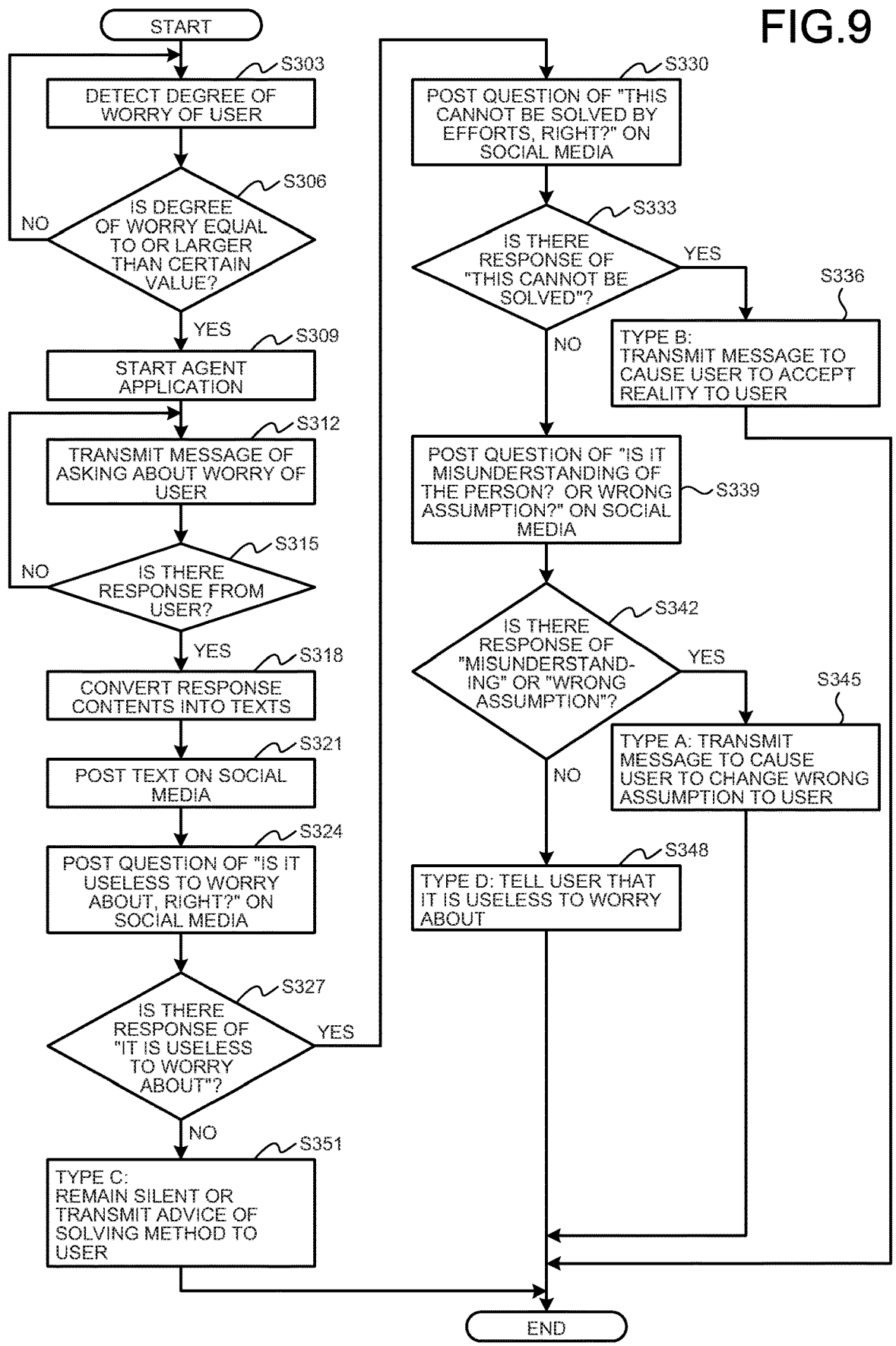
FIG. 9 is a flowchart illustrating an example of operation processing according to a third embodiment.

FIG. 9 is a flowchart illustrating an example of operation processing according to the present embodiment. As illustrated in FIG. 9, first, the server 2 detects the degree of worry of the user (Step S303), and when the degree of worry is equal to or larger than a certain value (Step S306/Yes), the server 2 starts the agent application on the information processing terminal 1 (Step S309).

Next, the server 2 presents a message from the information processing terminal 1 to the user to ask about the user's worry (Step S312).

Next, when there is a response from the user (Step S315/Yes), the server 2 converts the response content into text (Step S318) and posts the text on social media (Step S321).

Next, the server 2 asks a question on the social media, "This is useless to worry about, right?" (Step S324).

Next, when there is a reply saying "It is useless to worry about" (Step S327/Yes), the server 2 asks the question "This cannot be solved by efforts, right?" on social media (Step S330).

Next, when there is a response that "This cannot be solved." (Step S333/Yes), the server 2 transmits a message of type B to the user to accept the reality (Step S336).

On the other hand, when there is no reply that "This cannot be solved" (Step S333/No), the server 2 asks the question "Is it misunderstanding of the person? Or wrong assumption?" on the social media (Step S339).

Next, when there is a response of "Misunderstanding" or "Wrong assumption" (Step S342/Yes), a message of type A to change the assumption is transmitted to the user (Step S345).

Next, when there is no reply of "Misunderstanding" or "Wrong assumption" response (Step S342/No), the server 2 transmits a message of type D (almighty message) that it is useless to worry about (step S348).

Further, in the above Step S327, when there is no reply of "It is useless to worry about" (Step S327/No), the server 2 is silent (no message), or transmits a message of type C such as advice on a solution to the user (Step S351).

The server 2 can construct a database for automatic recognition of worry cause classification by repeatedly asking users of many social media about Steps S327 to S342.

Further, for social media users, by incentives such as accumulating points when answering questions and being treated preferentially when they receive services, an environment where they can actively answer questions may be prepared.

The operation processing of the third embodiment has been specifically described above.

3-4. Fourth Embodiment

Basically, for the advice that the user is notified of, it is assumed that a message in a gentle tone that eliminates unpleasant feelings such as user's anxiety, regret, or hesitation is transmitted in order to relieve the user from worries. However, in some cases, a harsh tone of message is useful.

Table 8 below illustrates an example of a harsh tone message.

TABLE 8

| No. | Worry cause | Message type | Message example |
|---|---|---|---|
| 3-1 | Want to get back together with ex-girlfriend | Type A | "You were dumped by her, don't you have some wrong assumption?" |
| 3-2 | Regret not being with parent when he/she passes away | Type B | "Accept reality that she has left!" |
| 3-3 | If I had studied harder, I could have enter that college | Type B | "Accept reality that you failed" |
| ... | ... | | |

The server 2 may appropriately switch between a gentle message and a harsh message according to the personality and taste of the user. Further, the server 2 may switch the message depending on the situation of the user at that time. Further, when it is not possible to determine which message influences the change of the user's thought, the server 2 may transmit a message at random.

Further, the server 2 may also learn which message has influenced the user's thought. Hereinafter, a specific description will be given with reference to FIG. 10.

Figure 10:
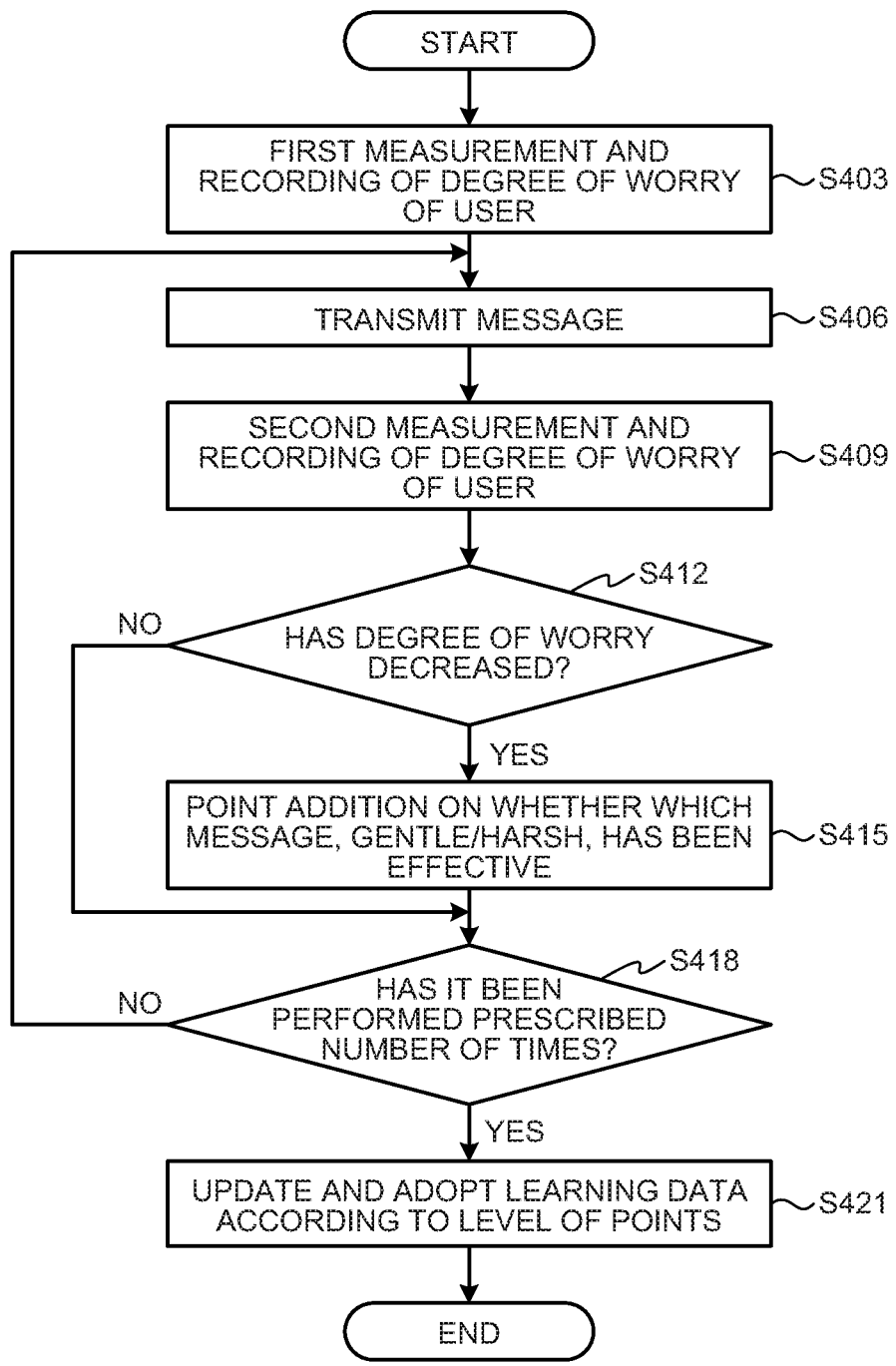
FIG. 10 is a flowchart illustrating an example of operation processing according to a fourth embodiment.

FIG. 10 is a flowchart illustrating an example of operation processing according to the present embodiment. As illustrated in FIG. 10, first, the server 2 performs first measurement and recording of the degree of worry of the user (Step S403).

Next, the server 2 transmits a message according to the degree of worry and the worry cause (Step S406). At this time, a gentle/harsh message may be randomly selected and transmitted. Further, the server 2 records how many times a gentle/harsh message is transmitted.

Next, the server 2 performs second measurement and recording of the degree of worry of the user (Step S409). At this time, the server 2 may transmit a harsh message when a gentle message has been transmitted at the first time, and may transmit a gentle message when a harsh message has been transmitted.

Next, it is determined whether the degree of worry has decreased after the first message transmission and after the second message transmission. (Step S412)

Next, when the degree of worry has decreased (Step S412/Yes), the server 2 adds a point to a predetermined list as to which message, gentle/harsh, has been effective (Step S415).

Next, when the processing indicated in Steps S406 to S415 have been performed the prescribed number of times (Step S418), the server 2 updates and adopts learning data according to the level of points (Step S421). When an approach is effective for one worry, a similar approach can be expected to be effective for other worries.

Note that the server 2 can similarly learn whether or not there is an effect for, the frequency of the message, the length of explanation of the reason for the message, and the like, in addition to the message type (gentle/harsh).

Table 9 below illustrates an example of a gentle message and a harsh message according to the message type corresponding to the worry cause.

TABLE 9

| Worry cause | Message type | Gentle message | Harsh message |
|---|---|---|---|
| Want to get back together with ex-girlfriend | Type A | "Do you think she wants to get back together?" | "You were dumped by her, don't you have some wrong assumption?" |
| Regret not being with parent when he/she passes away | Type B | "There was no way to see him/her" | "Accept reality that she has left!" |
| If I had studied harder, I could have enter that college | Type B | "There was no way not to fail" | "Accept reality that you failed" |
| . . . | . . . | . . . | . . . |

The operation processing of the fourth embodiment has been specifically described above.

3-5. Fifth Embodiment

Subsequently, a case where the present system is applied to a small community such as home, school, and workplace will be described. It is expected that this system is particularly effective in solving events that tend to occur in situations where a plurality of members belong, such as when recognition of reality is wrong.

For example, in the same workplace, when user A and user B bother each other with false recognition and are each worried about it, in this system, a message that points out false recognition is transmitted to both of them, and therefore, it is possible to solve the worry more effectively. Table 10 below illustrates an example of the type of worry in this case and the corresponding message.

TABLE 10

| Worry cause | | Message type | Message example |
|---|---|---|---|
| User A | Although I am kind to tell it, B does not hear what I say! B is insolent. | Type A | "It seems that B tries to work hard by himself/herself" |
| User B | Although I am working so hard, A talks to me insistently and annoyingly. Too annoying! | Type A | "It seems that A is kind to tell that" |

The cause of worry is an example of an answer obtained by asking the cause of worry, such as "Is there something?" from the agent, when the worry situation of the user is detected. From the contents of this answer, it is possible to create an effective message to cause them to understand that they were confused with each other, and solving their worries, so that a greater effect can be expected.

Figure 11:
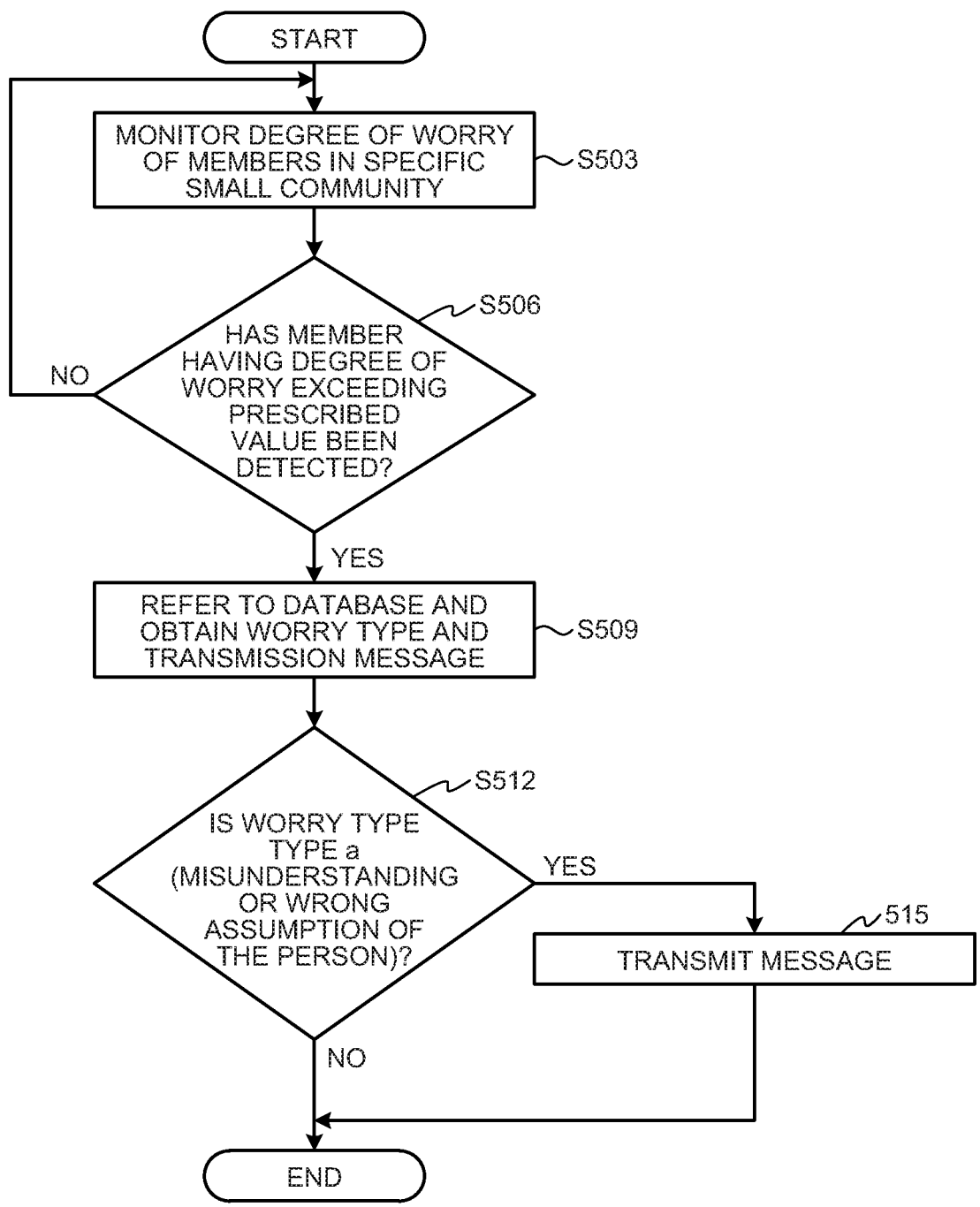
FIG. 11 is a flowchart illustrating an example of operation processing according to a fifth embodiment.

FIG. 11 is a flowchart illustrating an example of operation processing according to an embodiment. As illustrated in FIG. 11, first, the server 2 monitors the degree of worry of members of a specific small community (Step S303), and when a member having a worry that exceeds a specified value has been detected (Step S506/Yes), the server refers to the database, and obtains the worry type and a message to be transmitted (Step S509). Here, FIG. 12 illustrates an example of the worry type and the corresponding message. For the worry type, it may be determined whether it is type a: the worry is from misunderstanding or wrong assumption of the person, or type b; the worry cannot be solved by the efforts of the person.

Next, when the worry type is type a (misunderstanding or wrong assumption of the person) (Step S512/Yes), the server 2 transmits a message to the user (Step S515).

3-6. Supplement

Each of the embodiments described above is a system for notifying a message so that, when the user's worry situation (by behavior, verbal behavior, body reaction, sleep situation) is equal to or larger than a certain level, the worry is solved. However, the present embodiment is not limited to the detection of a worry, and it is also possible to automatically detect a problem from the user situation.

The server 2 may publish the automatically detected task on, for example, social media, and present the user with a message generated based on a response obtained from the social media.

For example, when recognizing that the weight of the user is increased rapidly recently, the server 2 may post a question on the social media, "Weight is rapidly increased recently. What kind of diet method is better?", notify the user of the upper diet method with the most answers, and prompt the user to change his/her behavior.

4. SUMMARY

As described above, the information processing system according to the embodiment of the present disclosure can detect the worry and notify the user of a message.

Although the preferred embodiment of the present disclosure has been described above in detail with reference to the appended drawings, the present technology is not limited to this example. It is obvious that a person with an ordinary skill in a technological field of the present disclosure could conceive of various alterations or corrections within the scope of the technical ideas described in the appended claims, and it should be understood that such alterations or corrections will naturally belong to the technical scope of the present disclosure.

For example, it is also possible to create a computer program for causing hardware such as the CPU, the ROM, the RAM, and the like, embedded in the information processing terminal 1 or the server 2 described above to exert a function of the information processing terminal 1 or the server 2. Further, a computer-readable storage medium storing the computer program is also provided.

Furthermore, the effects described in the present specification are merely illustrative or exemplary and are not restrictive. That is, the technology according to the present disclosure can exhibit other effects obvious to those skilled in the art from the description of the present specification in addition to or in place of the above-described effects.

Note that the present technology can also have the following configurations.

(1) An information processing system comprising
a control unit that performs control to
estimate at least one of a worry cause of a user and a degree of worry of the user based on sensing data related to the user, and
present a message to the user when at least one of the worry cause and the degree of worry satisfies a specific condition.

(2) The information processing system according to (1),
wherein the control unit
performs control to present the message to the user when the worry cause matches a specific cause or classification of the specific cause.

(3) The information processing system according to (1) or (2),
wherein the control unit
performs control to switch contents of the message presented to the user according to classification of the worry cause.

(4) The information processing system according to (3),
wherein the control unit
controls an agent that can interact with the user and can transmit and receive information to and from registered users in a specific social media,
classifies a worry cause of the user that is obtained by the agent by interaction with the user based on an answer obtained by asking the registered users in the specific social media, and
performs control to present a message to the user according to the classification.

(5) The information processing system according to (3) or (4),
wherein the control unit
performs control to switch the contents of the message presented to the user according to
whether the worry cause is that reality recognition of the user is not valid, or
even if the reality recognition of the user is valid, the worry cannot be solved by the user.

(6) The information processing system according to any one of (3) to (5),
wherein the control unit
learns a relationship between the worry cause of the user and the classification of the worry cause in advance, and
performs control to estimate the classification based on the worry cause of the user, and present the message to the user according to the classification.

(7) The information processing system according to any one of (1) to (6),
wherein the control unit
performs control to present the message to the user when the degree of worry exceeds a specific threshold.

(8) The information processing system according to (7),
wherein the control unit
registers the worry cause as a specific cause of which message is to be presented when the degree of worry exceeds the specific threshold.

(9) The information processing system according to any one of (1) to (8),
wherein the control unit
estimates the worry cause of the user or the degree of worry of the user based on a specific feature amount obtained from the sensing data related to the user.

(10) The information processing system according to any one of (1) to (9),
wherein the control unit
performs control to present one of a plurality of types of messages to the user.

(11) The information processing system according to (10),
wherein the control unit
presents one of the plurality of types of messages according to an attribute of the user.

(12) The information processing system according to (10),
wherein the control unit
presents one of the plurality of types of messages according to a situation of the user.

(13) The information processing system according to (10),
wherein the control unit
presents one of the plurality of types of messages to the user, and then monitors a change in the degree of worry of the user to learn an optimal message for the user.

(14) An information processing method, by a processor, comprising
performing control to
estimate at least one of a worry cause of a user and a degree of worry of the user based on sensing data related to the user, and
present a message to the user when at least one of the worry cause and the degree of worry satisfies a specific condition.

(15) A recording medium in which a program is recorded, the program for causing
a computer to function as a control unit that performs control to
estimate at least one of a worry cause of a user and a degree of worry of the user based on sensing data related to the user, and
present a message to the user when at least one of the worry cause and the degree of worry satisfies a specific condition.

REFERENCE SIGNS LIST

1 INFORMATION PROCESSING TERMINAL
2 SERVER
3 NETWORK
100 CONTROL UNIT
110 COMMUNICATION UNIT
120 INPUT UNIT
121 OPERATING INPUT UNIT
122 SENSOR
130 OUTPUT UNIT
131 DISPLAY UNIT
132 SPEAKER
140 STORAGE UNIT
200 CONTROL UNIT
201 DATA ANALYSIS UNIT
202 DEGREE OF WORRY DETECTION UNIT
203 WORRY CAUSE ESTIMATION UNIT
204 MESSAGE PRESENTATION CONTROL UNIT
210 COMMUNICATION UNIT
220 STORAGE UNIT

The invention claimed is:

1. An information processing system, comprising:
a control unit configured to:
estimate at least one of a first worry cause of a user or a degree of worry of the user based on sensing data related to the user,
classify the first worry cause based on determination that the first worry cause matches a specific cause,
control to present a message to the user based on the classification of the first worry cause,
determine a change in the estimated degree of worry of the user based on the presented message, and
switch a tone to present the message to the user based on the determined change in the degree of worry.

2. The information processing system according to claim 1, wherein the control unit is further configured to switch contents of the message based on the classification of the first worry cause.

3. The information processing system according to claim 2, wherein the control unit is further configured to:
control an agent, wherein the agent is configured to:
interact with the user, transmit information to and from a plurality of registered users in a specific social media, and
receive information to and from the plurality of registered users in the specific social media,
classify a second worry cause of the user based on an answer of the plurality of registered users in the specific social media, wherein the second worry cause is based on an interaction of the agent with the user, and
control to present the message to the user based on the classification of the second worry cause.

4. The information processing system according to claim 2, wherein the control unit is further configured to:
switch the contents of the message based on:
determination that a reality recognition of the first worry cause of the user is not valid, or
determination that the reality recognition of the user is valid and a worry corresponding to the first worry cause is not solvable by the user.

5. The information processing system according to claim 2, wherein the control unit is further configured to:
acquire a relationship between the first worry cause of the user and the classification of the first worry cause,
estimate the classification based on the first worry cause of the user, and
present the message to the user based on the classification.

6. The information processing system according to claim 1, wherein the control unit is further configured to present the message to the user based on determination that the degree of worry exceeds a specific threshold.

7. The information processing system according to claim 6, wherein the control unit is further configured to register the first worry cause as the specific cause based on the determination that the degree of worry exceeds the specific threshold.

8. The information processing system according to claim 1, wherein the control unit is further configured to estimate at least one of the first worry cause of the user or the degree of worry of the user based on a specific feature amount of the sensing data.

9. The information processing system according to claim 1, wherein the control unit is further configured to present one of a plurality of types of messages to the user.

10. The information processing system according to claim 9, wherein the control unit is further configured to present one of the plurality of types of messages based on an attribute of the user.

11. The information processing system according to claim 9, wherein the control unit is further configured to present one of the plurality of types of messages based on a situation of the user.

12. The information processing system according to claim 9, wherein the control unit is further configured to:
present one of the plurality of types of messages to the user, and
monitor the change in the degree of worry of the user to acquire an optimal message for the user.

13. An information processing method, comprising:
estimating, by a processor, at least one of a worry cause of a user or a degree of worry of the user based on sensing data related to the user,
classifying, by the processor, the worry cause based on determination that the worry cause matches a specific cause,
controlling to present, by the processor, a message to the user based on the classification of the worry cause,
determining, by the processor, a change in the estimated degree of worry of the user based on the presented message, and
switching, by the processor, a tone to present the message to the user based on the determined change in the degree of worry.

14. A non-transitory computer-readable medium having stored thereon, computer-executable instructions which, when executed by a computer, cause the computer to execute operations, the operations comprising:
estimating at least one of a worry cause of a user or a degree of worry of the user based on sensing data related to the user,
classifying the worry cause based on determination that the worry cause matches a specific cause,
presenting a message to the user based on the classification of the worry cause,
determining a change in the estimated degree of worry of the user based on the presented message, and
switching a tone to present the message to the user based on the determined change in the degree of worry.

* * * * *